US012682985B2

(12) United States Patent
Siepe et al.

(10) Patent No.: US 12,682,985 B2
(45) Date of Patent: Jul. 14, 2026

(54) COMPUTER-IMPLEMENTED METHOD FOR PROVIDING TRAINING DATA FOR A MACHINE LEARNING ALGORITHM FOR CLASSIFYING PLANTS INFESTED WITH A PATHOGEN

(71) Applicant: BASF SE, Ludwigshafen am Rhein (DE)

(72) Inventors: Isabella Siepe, Limburgerhof (DE); Kristina Busch, Limburgerhof (DE); Till Eggers, Ludwigshafen (DE); Ramon Navarra-Mestre, Limburgerhof (DE); Egon Haden, Speyer (DE); Jessica Arnhold, Alfter (DE); Sebastian Fischer, Limburgerhof (DE); Andres Martin Palma, Utrera (ES); Christian Klukas, Limburgerhof (DE); Swetlana Friedel, Ludwigshafen (DE); Bastian Stuermer-Stephan, Ottersberg (DE); Stefan Hahn, Limburgerhof (DE); Stefan Tresch, Limburgerhof (DE)

(73) Assignee: BASF SE, Ludwigshafen am Rhein (DE)

( * ) Notice: Subject to any disclaimer, the term of this patent is extended or adjusted under 35 U.S.C. 154(b) by 287 days.

(21) Appl. No.: 18/036,121

(22) PCT Filed: Nov. 12, 2021

(86) PCT No.: PCT/EP2021/081542
§ 371 (c)(1),
(2) Date: May 9, 2023

(87) PCT Pub. No.: WO2022/101419
PCT Pub. Date: May 19, 2022

(65) Prior Publication Data
US 2024/0021273 A1      Jan. 18, 2024

(30) Foreign Application Priority Data

Nov. 12, 2020    (EP) ..................................... 20382978

(51) Int. Cl.
G16B 40/00          (2019.01)
G06V 10/82          (2022.01)
(Continued)

(52) U.S. Cl.
CPC .............. G16B 40/00 (2019.02); G06V 10/82 (2022.01); G06V 20/188 (2022.01); G06V 20/70 (2022.01)

(58) Field of Classification Search
CPC ...... G16B 40/00; G06V 10/82; G06V 20/188; G06V 20/70; G06V 10/58; G06V 20/693; G06V 20/698
See application file for complete search history.

(56) References Cited

U.S. PATENT DOCUMENTS

2017/0131200 A1* 5/2017 Raveh ..................... G01N 21/21
2020/0017924 A1* 1/2020 Hogan ..................... G16B 25/10
(Continued)

FOREIGN PATENT DOCUMENTS

WO      WO-2017194276 A1 * 11/2017 ............. G01N 21/27

OTHER PUBLICATIONS

Wang et al. (Detection of Huanglongbing (citrus greening) based on hyperspectral image analysis and PCR) (Year: 2019).*
(Continued)

*Primary Examiner* — Wassim Mahrouka
(74) *Attorney, Agent, or Firm* — ArentFox Schiff LLP

(57) ABSTRACT

Computer-implemented method for providing training data for a machine learning algorithm for image classifying a pathogen infestation of a plant, comprising the steps: providing image data of a plant or a plant part infested with a
(Continued)

| S10: providing image data of a plant or a plant part infested with a pathogen |
| :--- |
| S20: providing genetic result data of the plant or the plant part to which the image data referred comprising at least information about type of pathogen |
| S30: labeling the image data with the genetic result data | pathogen; providing genetic result data of the plant or the plant part to which the image data referred comprising at least information about the type of pathogen; labeling the image data with the genetic result data.

17 Claims, 2 Drawing Sheets

(51) Int. Cl.
G06V 20/10 (2022.01)
G06V 20/70 (2022.01)

(56) References Cited

U.S. PATENT DOCUMENTS

| | | | | |
|---|---|---|---|---|
| 2020/0320682 | A1* | 10/2020 | Alexander | G01N 21/27 |
| 2021/0209747 | A1* | 7/2021 | Jung | G06T 7/0004 |
| 2022/0196564 | A1* | 6/2022 | Wolf | G01N 21/94 |
| 2023/0333011 | A1* | 10/2023 | Dev | G01J 3/2823 |

OTHER PUBLICATIONS

International Search Report and Written Opinion of International Application No. PCT/EP2021/081542 mailed Feb. 28, 2022, 8 pgs.
De Melo et al., "Diagnosis of Apple Fruit Diseases in the Wild with Mask R-CNN", Foundations of Augmented Cognition: 7th International Conference, Oct. 13, 2020, Springer Nature, Switzerland, AG, pp. 256-270.
Sankaran et al., "A review of advanced techniques for detecting plant diseases", Computers and Electronics in Agriculture, Jun. 1, 2010, vol. 72, No. 1, ELSEVIER, Amsterdam, NL, pp. 1-13.
Yuan et al., "Crop Disease Image Classification Based on Transfer Learning with DCNNs", Advances in Databased and Information Systems, Springer, Nov. 2, 2018, pp. 457-468.
European Search Report for Application No. EP 20382978.3 dated Apr. 27, 2021, 8 pgs.

* cited by examiner

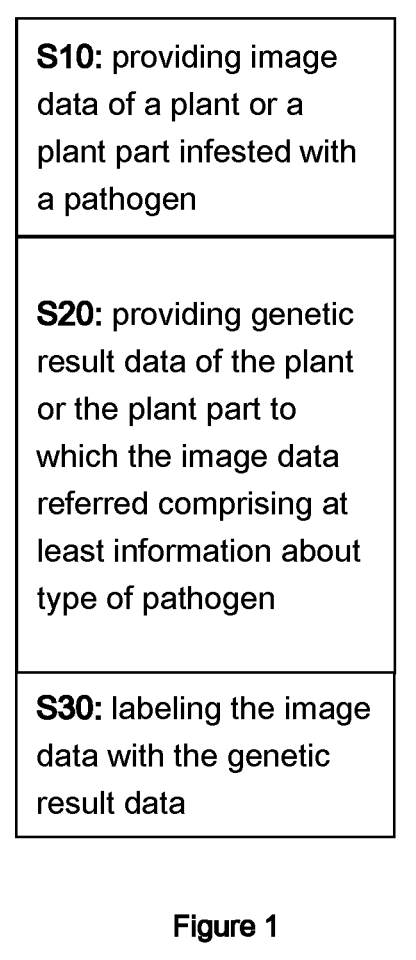

S10: providing image data of a plant or a plant part infested with a pathogen

S20: providing genetic result data of the plant or the plant part to which the image data referred comprising at least information about type of pathogen

S30: labeling the image data with the genetic result data

Figure 1

COMPUTER-IMPLEMENTED METHOD FOR PROVIDING TRAINING DATA FOR A MACHINE LEARNING ALGORITHM FOR CLASSIFYING PLANTS INFESTED WITH A PATHOGEN

TECHNICAL FIELD

The present disclosure relates to a computer-implemented method for providing training data for a machine learning algorithm for image classifying a pathogen infestation of a plant.

TECHNICAL BACKGROUND

Pathogens, in particular fungal diseases, are a major problem in commercial agricultural production processes. For many processes, it is important to detect the pathogens as early as possible in order to be able to initiate respective countermeasures, such as treatment with fungicides, as early as possible. Infestation assessments of plant diseases have been carried out visually for many years and require very experienced phytopathologists who can recognize and differentiate the symptoms of the various diseases. Since the visual assessment is influenced by a wide range of biotic and abiotic factors, incorrect assessments cannot be excluded a. Furthermore, even a very experienced phytopathologists is able to detect many diseases only after a certain degree of infestation, so that an early stage infestation is often not detected. Moreover, the classification of the degree of infestation by phytopathologists suffers from the subjective judgement of the individual. This is particularly problematic if statistically relevant effects are to be measured, especially effects that are not very pronounced such as fungicidal effects of fungicidal development candidates. The effect becomes even more pronounced if the infection data is gathered over a prolonged period by more than one phytopathologist. In this case, the standard deviation of the assessments is increased by the respective disease features that are differently ranked by the individuals.

In view of this, it is found that a further need exists to provide a possibility to detect a pathogen on a plant or a part of a plant, in particular a fungal disease, in an early stage infestation. Moreover, a further need exits to provide a method that can objectively classify the degree of infestation of a plant with high confidentiality and low standard deviation.

SUMMARY OF THE INVENTION

In view of the above, it is an object of the present invention to provide a possibility to detect a pathogen on a plant or a part of a plant, in particular a fungal disease, in an early stage infestation.

A further object of the present invention is to provide a method that can objectively classify the degree of infestation of a plant with high confidentiality and low standard deviation.

These and other objects, which become apparent upon reading the following description, are solved by the subject matter of the independent claims. The dependent claims refer to preferred embodiments of the invention.

According to a first aspect of the present disclosure, a computer-implemented method for providing training data for a machine learning algorithm for image classifying a pathogen infestation of a plant is provided, comprising the steps: providing image data of a plant or a plant part infested with a pathogen; providing genetic result data of the plant or the plant part to which the image data referred comprising at least information about type of pathogen; labeling the image data with the genetic result data with respect to the pathogen, in particular as concentration, e.g. in relation to plant DNA, mass of plant leaves, etc.

The present disclosure is based on the finding that it is in principle possible to train a machine learning algorithm in such a way that it can reliably detect pathogens, even at an early stage of infestation, by analyzing image data of a plant or part of a plant, and classify the image data according to the extent of the disease. However, it has turned out that such a machine learning algorithm can only make a reliable classification, if the training data are highly reliable. It has also been shown that such a trained machine learning algorithm, e.g. a neural network, in many cases, can detect a pathogen more reliably and earlier than a human being. In order to provide such reliable training data, the present disclosure proposes to provide image data of infested plants and to carry out a genetic analysis, e.g. a DNA and/or a RNA analysis, of these plants. This makes it possible to provide training data of very high quality, which can be labelled with virtually no errors. It has been shown that with such training data a machine learning algorithm can be trained, which in many cases can classify images of infested plants more reliably than a human being. However, it should be noted that the present disclosure is not limited to the fact that only the genetic result data are used for providing the training data. In fact, in addition other data/parameters can be used additionally for labelling the image data.

In this context, it should be noted that the training data obtained according to the present disclosure could be used as training data for different machine learning algorithms, e.g. deep learning model, neural networks with different structures, etc. The image data can be provided in different formats and/or be provided from different images and/or partial images of plants and/or from different plant parts. The genetic result data can be obtained by different genetic analysis methods. In this context, it is only important that the genetic result data are based on the plant or plant part referenced in the respective image data. Notably, in this context, it is only important that the image data are unambiguously assigned to the respective genetic result data, e.g. DNA and/or RNA result data, so that an error-free labeling of the training data can take place. The term pathogen is understood broadly as any living organism, which can cause harm to a plant or can negatively affect the growth or the health of a plant. Pathogens include, but are not limited to, any kinds of weeds, fungi, bacteria, viruses, insect pests, arachnids, nematodes, mollusks, and rodents. In this respect, it is only relevant that such pathogen may be detected, at least in one infestation stage, by means of an image analysis. Preferably, pathogens include fungi, bacteria, viruses, insect pests, arachnids, nematodes, mollusks, and rodents. More preferably, pathogens include fungi, bacteria, and viruses. In an example, the pathogen is a fungus, in particular the *Phakopsora pachyrhizi* fungus. Such a *Phakopsora pachyrhizi* fungus may affect different plant species, wherein in an example, the plant is a soybean plant and the fungus is *Phakopsora pachyrhizi*.

The "type of pathogen" includes, but is not limited to, any classification of the pathogen as such and/or of its growth stage(s). Preferably, the "type of pathogen" includes any biological classification of the pathogen. More preferably, the "type of pathogen" includes class, subclass, order, family, genus, species, subspecies, variety, biotype, and mutant of the pathogen. Most preferably, the "type of pathogen"

includes species, subspecies, variety, biotype, and mutant of the pathogen. Particularly, the "type of pathogen" additionally includes the biological classification of the pathogen as well as the classification of its growth stage(s).

"Plant part" or "part of a plant" includes, but is not limited to, leaves, cotyledones (seed leaves), roots, stems, flowers, fruits, pollens, xylem, phloem, seeds. Preferably, "plant part" or "part of a plant" include any above-ground parts of a plant. More preferably, "plant part" or "part of a plant" include leaves, cotyledones (seed leaves), stems, flowers, and fruits. Most preferably, "plant part" or "part of a plant" include leaves, cotyledones (seed leaves), and fruits. Particularly, "plant part" or "part of a plant" include leaves and cotyledones (seed leaves).

The invention is particularly suitable for the following combinations of pathogens on plants or plant parts: *Albugo* spp. (white rust) on ornamentals, vegetables (e. g. *A. candida*) and sunflowers (e. g. *A. tragopogonis*); *Alternaria* spp. (*Alternaria* leaf spot) on vegetables (e.g. *A. dauci* or *A. porri*), oilseed rape (*A. brassicicola* or *brassicae*), sugar beets (*A. tenuis*), fruits (e.g. *A. grandis*), rice, soybeans, potatoes and tomatoes (e. g. *A. solani, A. grandis* or *A. alternata*), tomatoes (e. g. *A. solani* or *A. alternata*) and wheat (e.g. *A. triticina*); *Aphanomyces* spp. on sugar beets and vegetables; *Ascochyta* spp. on cereals and vegetables, e. g. *A. tritici* (anthracnose) on wheat and *A. hordei* on barley; *Aureobasidum zeae* (syn. *Kapateiella zeae*) on corn; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Eysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages); *B. squamosa* or *B. allii* on onion family), oilseed rape, ornamentals (e.g. *B. eliptica*), vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladobotryum* (syn. *Dactylium*) spp. (e.g. *C. mycophlium* (formerly *Dactylium dendroides*, teleomorph: *Nectria albertinii, Nectria rosella* syn. *Hypomyces rosellus*) on mushrooms; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes* black dot), beans (e. g. *C. lindemuthianum*), soybeans (e. g. *C. truncatum* or *C. gloeosporioides*), vegetables (e.g. *C. lagenarium* or *C. capsici*), fruits (e.g. *C. acutatum*), coffee (e.g. *C. coffeanum* or *C. kahawae*) and *C. gloeosporioides* on various crops; Corticium spp., e. g. *C. sasakii* (sheath blight) on rice; *Corynespora cassiicola* (leaf spots) on soybeans, cotton and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Demato-*

*phora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (formerly *Phaeoacremonium chlamydosporum*), *Phaeoacremonium aleophllum* and/or *Botryosphaeria obtusa*, *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, oilseed rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticilliodes* on corn; *Gaeurmannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwelli* (black rot) on vines; *Gymnosporangium* spp. on rosaceous plants and junipers, e. g. *G. sabinae* (rust) on pears; *Helminthasporium* spp. (syn. *Drechslera*, teleomorph: *Cochliobolus*) on corn, cereals, potatoes and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (syn. *Monilia* spp.: bloom and twig blight, brown rot) on stone fruits and other rosaceous plants; *Mycosphaerella* spp. on cereals, bananas, soft fruits and ground nuts, such as e. g. *M. graminicola* (anamorph: *Zymoseptoria tritici* formerly *Septoria tritici*: *Septoria* blotch) on wheat or *M. fijiensis* (syn. *Pseudocercospora fijiens*: black Sigatoka disease) and *M. musicola on bananas, M. arachidicola* (syn. *M. arachidis* or *Cercaspora arachidis*), *M. berkeleyi* on peanuts, *M. pisi* on peas and *M. brassiciola* on brassicas; *Peronospora* spp. (downy mildew) on cabbage (e. g. *P. brassicae*), oilseed rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (syn. *Leptosphaeria biglobosa* and *L. maculans*: root and stem rot) on oilseed rape and cabbage, *P. betae* (root rot, leaf spot and damping-off) on sugar beets and *P. zeae-maydis* (syn. *Phyllostica zeae*) on corn; *Phomopsis* spp. on sunflowers, vines (e. g. *P. viticola*: can and leaf spot) and soybeans (e. g. stem rot: *P. phaseloi*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P.*

*capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, oilseed rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits (e. g. *P. leucotricha* on apples) and curcurbits (*P. xanthii*); *Polymyxa* spp., e. g. on cereals, such as barley and wheat (*P. graminis*) and sugar beets (*P. betae*) and thereby transmitted viral diseases; *Pseudocercosporella herpotrichoides* (syn. *Oculimacula yallundae*, *O. acuformis*: eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenopeziza* spp., e.g. *P. brassicae* on oilseed rape; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*: rice blast) on rice and *P. grisea* on turf and cereals; *Pythium* spp. (damping-off) on turf, rice, corn, wheat, cotton, oilseed rape, sunflowers, soybeans, sugar beets, vegetables and various other plants (e. g. *P. ultimum* or *P. aphanidermatum*) and *P. oligandrum* on mushrooms; *Ramularia* spp., e. g. *R. collocygni* (*Ramularia* leaf spots, Physiological leaf spots) on barley, *R. areola* (teleomorph: *Mycosphaerella areola*) on cotton and *R. beticola* on sugar beets; *Rhizoctonia* spp. on cotton, rice, potatoes, turf, corn, oilseed rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* and *R. commune* (scald) on barley, rye and triticale; *Sarocladium oryzae* and *S. attenuatum* (sheath rot) on rice; *Sclerotinia* spp. (stem rot or white mold) on vegetables (*S. minor* and *S. sclerotiorum*) and field crops, such as oilseed rape, sunflowers (e. g. *S. sclerotiorum*) and soybeans, *S. rolfsii* (syn. *Athela rolfsii*) on soybeans, peanut, vegetables, corn, cereals and ornamentals; *Septoria* spp. on various plants, e. g. *S. glycines* (brown spot) on soybeans, *S. tritici* (syn. *Zymoseptoria tritici*, *Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setosphaeria* spp. (leaf blight) on corn (e. g. *S. turcicum*, syn. *Helminthosporium turcicum*) and turf; *Sphacelotheca* spp. (smut) on corn, (e. g. *S. reiliana*, syn. *Ustilago reiliana*: head smut), sorghum und sugar cane; *Sphaerotheca fuliginea* (syn. *Podosphaera xanthii*: powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*, syn. *Septoria nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara*

*elegans*); *Tilletia* spp. (common bunt or stinking smut) on cereals, such as e. g. *T. tritici* (syn. *T. caries*, wheat bunt) and *T. controversa* (dwarf bunt) on wheat; *Trichoderma harzianum* on mushrooms; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*), sugar beets (e. g. *U. betae* or *U. beticola*) and on pulses (e.g. *U. vignae*, *U. pisi*, *U. viciae-fabae* and *U. fabae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. longisporum* on oilseed rape, *V. dahliae* on strawberries, oilseed rape, potatoes and tomatoes, and *V. fungicola* on mushrooms; *Zymoseptoria tritici* on cereals.

The compounds I and compositions thereof, respectively, are particularly suitable for controlling the following causal agents of plant diseases: rusts on soybean and cereals (e.g. *Phakopsora pachyrhizi* and *P. meibomiae* on soy; *Puccinia tritici* and *P. striiformis* on wheat); molds on specialty crops, soybean, oil seed rape and sunflowers (e.g. *Botrytis cinerea* on strawberries and vines, *Sclerotinia sclerotiorum*, *S. minor* and *S. rolfsii* on oil seed rape, sunflowers and soybean); *Fusarium* diseases on cereals (e.g. *Fusarium culmorum* and *F. graminearum* on wheat); downy mildews on specialty crops (e.g. *Plasmopara viticola* on vines, *Phytophthora infestans* on potatoes); powdery mildews on specialty crops and cereals (e.g. *Uncinula necator* on vines, *Erysiphe* spp. on various specialty crops, *Blumeria graminis* on cereals); and leaf spots on cereals, soybean and corn (e.g. *Septoria tritici* and *S. nodorum* on cereals, *S. glycines* on soybean, *Cercospora* spp. on corn and soybean).

In an embodiment, the genetic result data further comprises information about the extent of the pathogen infestation, wherein the information about the extent of the infestation can be provided in different units/formats as long as this allows a quantification of the infestation, e.g. such as the amount of genetic material per biomass, amount of colony-forming units per biomass etc., i.e. any information which allows a direct or indirect quantified conclusion on the grade of infestation. The additional quantitative information on the extent to which the plants and/or plant parts, shown in the image data, are infested with a pathogen can further improve the quality of the training data. Moreover, this may make it possible that a machine learning algorithm, e.g. a deep learning algorithm, trained with such training data may also estimate the extent of infestation when analyzing image data, i.e. in this example, not only the information may be outputted whether and which pathogen infestation may be at hand, but also an estimation of the extent of the pathogen infestation may be outputted.

In an embodiment, the image data is based on at least one RGB-image of the plant and/or the plant part, wherein the at least one RGB-image is preferably taken against a white background. Such RGB-images can be generated by a standard camera or mobile phone. However, it could also be (i) a hyperspectral image, preferably in a radiation range between 390 nm and 1650 nm, more preferably up to 850 nm and/or (ii) a multispectral image, in which the information density is much higher. Thus, alternatively or in addition, the image data may be based on at least one hyperspectral and/or multispectral image. The latter is preferably in the radiation range between about 390 nm and about 850 nm, in the near infrared range with about 800 nm and in the far infrared range (FIR) with about 820 nm, wherein the at least one multispectral image is preferably taken against a white background. In an example, the multispectral image was taken with at least three spectral channels. In one example, one spectral channel is in a visible spectral range, in a near infrared range and in a far infrared range. In a further example, the radiation range is adopted to a specific pathogen or other parameters, like the absorption maxima values of chlorophylls, e.g. which his for chlorophyll a in the red region at 642 nm and in the blue region at 372 nm and for chlorophyll b the values are 626 nm in the red region and 392 nm in the blue region.

In an example, it is possible to base the image data on nine images of the plant or plant part, wherein it is preferred that the image data is based on six side views and three top views of the plant or plant part. However, the present disclosure is not limited to any specific numbers of images used for providing the image data.

In an embodiment, the method further comprises the step of filtering the image(s), trimming and/or marking specific areas of the image(s) before providing the image data. This makes it possible to limit an analysis/the training data to only the relevant parts of a plant. For example, plant pots as well as non-infested primary leaves may be excluded from the data set, so that only the infested parts of the plant are considered.

The infestation of a plant can be tested by any genetic methods. This involves testing for the presence and preferably the quantity of genetic material in plant samples that can be attributed to a pathogen. In other words, the term genetic methods is to be understood broadly and encompasses any method by which the presence of a pathogen can be determined and preferably any method by which also the extent of the pathogen may be determined.

In an embodiment, the genetic result data is based on a DNA and/or a RNA analysis, like a sequencing method selected from the group of: PCR-based techniques, e.g. quantitative PCR ("qPCR"), isothermal amplification methods, e.g. loop-mediated amplification ("LAMP"), and/or a DNA analysis methods based on DNA-hybridization.

Over the recent years, promising DNA-analysis methods have become available, which may be applied in the context of the present disclosure: The loop-mediated isothermal amplification technology as first described in Nomi et al. (2000), Nucleic Acids Research, 28 (12), e63 does not require thermocycling equipment as conventionally needed for PCR analysis, and can be applied on-site, such as in the field. Several tests can be performed in parallel, e.g. in microarrays, and the analysis yields results within approximately 30 minutes.

Nanopore-sequencing, as described in Astier, Braha, and Bayley (2006) Journal of the American Chemical Society, 128 (5), 1705-10, or Fologea et al. (2005), *Nano Lett.* 5 (10), 1905-9., relies on the translocation of a DNA or RNA molecule through a nanopore. If an electric field is applied, an electric current can be observed, whose density across the nanopore surface depends on the nanopore*s dimensions and the composition of the nucleic acid that is passing through the nanopore. The pores are either provided by a protein, such as an alpha-hemolysin or a porin protein, or by solid state inorganic material. Nanopore-based analyses are fast, and several traits can be analyzed in parallel on the DNA- or RNA-level.

DNA-hybridization approaches use single stranded DNA- or RNA-probe molecules of typically 10-50 bases, which are immobilized to a surface and which are reverse complementary to a given target sequence. The readout can be accomplished electronically, or via optical methods, e.g. fluorescence. DNA-hybridization approaches can be conducted in microarrays as described in Miller & Tang (2009), Clinical Microbiology Reviews, and it is thus possible to analyze a sample on many traits, i.e. genetic sequences that convey a phenotype, in parallel. In general, DNA-hybridization technologies are highly suitable for parallelization, e.g. in microarrays, and ready-to-use microarrays can be applied on-site with acceptable analysis times and equipment requirements.

In summary, a variety of different technologies has emerged as second or third generation DNA-analysis means that can be parallelized, e.g. in microarrays, and only require minor to acceptable equipment, thereby enabling an in-situ analysis of a sample. They can thus be assembled in sensor devices that are capable of analyzing a multitude of genetic sequences in a sample of a plant or plant propagation material.

The present teachings can thus provide a method that can be carried out on-site, for example by a farmer or an agronomist, without any further shipping of samples. DNA-result data and information on pathogen infestation can thus be obtained within a timeframe of minutes rather than hours. The proposed teachings are particularly suitable for in-situ detection, i.e., measurement done essentially where the sample of the plant is collected. As used herein, the terms "in-situ" and "on-site" are equivalent and relate the situation that the measurement is performed essentially at the locus where the sample of the plant or the plant propagation material is collected and/or prepared. The same locus comprises both the immediate vicinity to the place where the sampling was carried out (e.g. within a radius of 1000 meters, such as within a radius of 100 meters), but may also relate to the functional or organizational unit where the sampling was carried out, such as a farm, a breeding station, a laboratory, a greenhouse etc.

Accordingly, DNA microarrays may be used in the present disclosure in which probe molecules are immobilized on a "chip". The sequence of the probe molecules is matched to the sequence of certain genes e.g. fungal pests. When a plant sample containing genetic material of a disease is applied to the chip, the pathogen DNA binds to the probe molecules and an optical or electrical signal may be generated. In particular, this technique can be used to test for certain fungicide-resistant fungal diseases. The fungicide resistance is often generated by genetic mutations/variations. These are known for many resistances, so that corresponding probe molecules are created and can be immobilized on the chips. By means of such genetic testing of plant material, for example for a fungal disease, such diseases can be detected long before external symptoms become visible. With the proposed genetic screening, training data can be provided, which can include a quantitative statement in addition to the qualitative statement, so that with such high-quality training data a well-functioning machine learning algorithm, e.g. an image classification algorithm, can also be obtained.

In an embodiment, the pathogen is a fungus, preferably a *Phakopsora pachyrhizi* fungus, wherein in an example, the plant is a soybean plant or a part thereof and the pathogen is a *Phakopsora pachyrhizi* fungus causing Asian soybean rust disease.

A further aspect of the present disclosure refers to a use of image data of a plant or a plant part infested with a pathogen in a method explained above. A further aspect of the present disclosure refers to a use of DNA result data of a plant or a plant part comprising at least information about a pathogen infestation in a method explained above. A further aspect of the present disclosure refers to a use of training test data obtained according to a method explained above for training a machine learning algorithm, e.g. a neural network or a deep learning model, for classifying image data.

A further aspect of the present disclosure refers to a machine learning algorithm, preferably a neural network, trained with training data provided according to a method described above. The training features for training the machine learning algorithm, e.g. the neural network, preferably comprise the Normalized Differences Vegetation Index (NDVI) and the Greeness Index (G). The Normalized Difference Vegetation Index quantifies vegetation by measuring the difference between near-infrared, which vegetation strongly reflects, and red light, which vegetation absorbs.

| Index | Indicator | Formula | Source |
|---|---|---|---|
| Normalized Difference Vegetation Index (NDVI) | Biomass Leaf Area | $NDVI = \dfrac{(R_{810} - R_{680})}{(R_{810} + R_{680})}$ | modified according to Rouse et al. (1974) |
| Greeness (G) | Chlorophyll | $G = \dfrac{Green}{Red}$ | modified according to Zarco-Tejada et al. (2005) |

A further aspect of the present disclosure refers to a classification system for image classifying a pathogen infestation of a plant, comprising: at least one input interface for providing image data of a plant or plant part; at least one evaluation unit which is set up to feed forward a machine learning algorithm with the image data of a plant or plant part, wherein the machine learning algorithm is trained on the basis of training data provided according to the method explained above; at least one output interface adapted to output a classification of a pathogen infestation of the plant. Such a system could be used by farmers to detect pathogen infestation, e.g. fungal infestation, before external signs become apparent. For example, the farmer can provide different images of a plant to be examined/classified. Moreover, such a system may also be used in the area of "greenhouse automation". Fungicides are tested in the greenhouse by treating infested plants and evaluating the results by means of a credit assessment. In an assessment, an employee manually evaluates the extent of damage to a plant and assigns it a percentage value. This process is naturally subjective and subject to strong fluctuations. Particularly in the case of active ingredient screenings with components that have not yet been optimized with regard to their fungicidal effect, it is difficult in this respect because the significance of the result for the given standard deviation does not always lead to a clear statement. Therefore, a classification system for image classifying a pathogen infestation of a plant may also be used in such application. In other words, the present disclosure provides the possibility that a farmer or an agronomic may take a picture or pictures of his field/plant, feed the trained machine learning algorithm and may then receive the information on pathogen infestation in-situ. Therefore, no shipping of a sample of the infected plant to a laboratory including a lag time in between measurement and information on infection status during which no treatment can occur can be entirely avoided.

A further aspect of the present disclosure refers to a computer-implemented method for image classifying a pathogen infestation of a plant, comprising the steps: providing image data of a plant or plant part; feeding a machine learning algorithm, e.g. a deep learning model, with the image data of a plant or plant part, wherein the machine learning algorithm is trained on the basis of training data provided according to the method explained above; outputting a classification of a pathogen infestation of the plant.

In an embodiment, the classification results of the pathogen infestation of the plant is used to provide a farmer a recommendation on how and with which active ingredient or crop protection product the infested plants may be treated. For example, a database comprising information about active ingredients and there field of application may be provided/used in which a respective query can be made in order to provide such a recommendation about the suitable active ingredient. In this respect, it is also possible that an automatic order for a suitable crop protection product is issued. In addition or as an alternative, it is also possible that based on the classification of the pathogen infestation other steps to be performed by a farmer are recommended in order to prevent a spread of the pathogen infestation in a field (e.g. use of a resistance crusher). In this respect, the present disclosure is not limited to a recommendation in view of the classification of the pathogen, but also further data may be considered (e.g. whether data, crop grow stage data, etc.).

In an embodiment, the classification of the pathogen infestation and/or the recommendation with respect to a treatment of the infested plants, an application map for an application device for applying a crop protection product on the field can be provided. In an example, it can be determined spatially distributed on a field whether and to what extent an infestation is present. Based on this data, it is possible to generate an application map for an application device (e.g. a sprayer, tractor, etc.) indicating/showing where and how much crop protection product is to be applied to the field. Moreover, it is also possible to generate control data for an application machine.

Finally, a further aspect of the present disclosure relates to a computer program element which when executed by a processor is configured to carry out a computer-implemented method for image classifying a pathogen infestation of a plant. The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments. This exemplary embodiment of the present disclosure covers both, a computer program that right from the beginning uses the present disclosure and computer program that by means of an update turns an existing program into a program that uses the present disclosure. Moreover, the computer program element might be able to provide all necessary steps to fulfill the procedure of an exemplary embodiment of the method as described above. According to a further exemplary embodiment of the present disclosure, a computer readable medium, such as a CD-ROM, USB stick or the like, is presented wherein the computer readable medium has a computer program element stored on it which computer program element is described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present disclosure, a medium for making a computer program element available for downloading is provided, which computer program element is arranged to perform a method according to one of the previously described embodiments of the present disclosure.

BRIEF DESCRIPTION OF THE DRAWINGS

In the following, the present disclosure is described exemplarily with reference to the enclosed figure, in which FIG. 1 is a schematic view of a method according to the preferred embodiment of the present disclosure.

DETAILED DESCRIPTION OF EMBODIMENT

Figure 2:
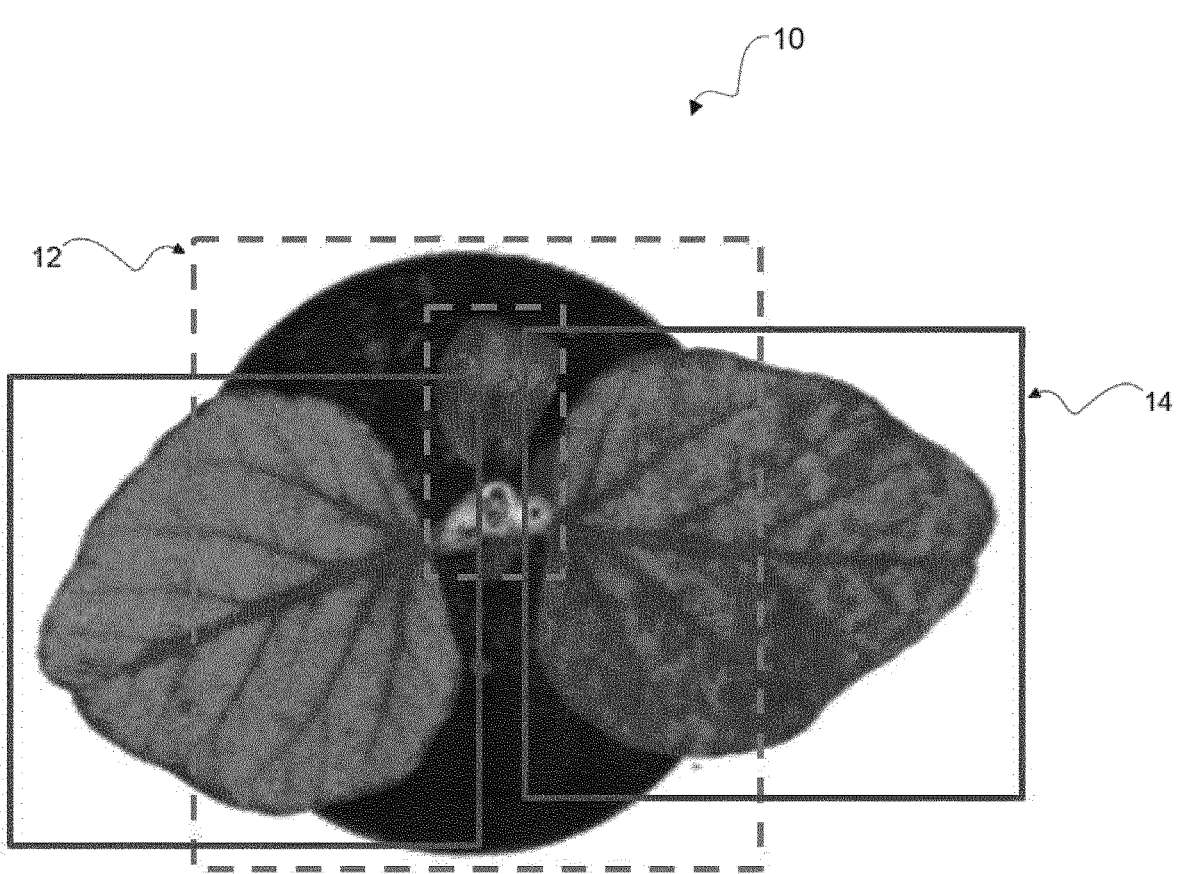
FIG. 2 is an exemplary schematic image, which may be used as basis for providing the image data.

FIG. 1 is a schematic view of a method according to the preferred embodiment of the present disclosure. In the following, an exemplary order of the steps according to the present disclosure is explained. However, the provided order is not mandatory, i.e. all or several steps may be performed in a different order or simultaneously.

The method described below can be summarized as follows. In a preparatory step, the plants to be analyzed, for example a soybean plant or a part thereof, are infected with a specific pathogen, for example *Phakopsora pachyrhizi* fungus causing Asian soybean rust. The infected plants or parts of these plants are then photographed to generate image data. Afterwards a genetic analysis with respect to the pathogen and preferably also with respect to the content of the pathogen of the photographed plant is determined, so that the image data can be combined with the results of the genetic analysis.

In a preferred embodiment, the image data is based on at least one RGB-image of the plant and/or the plant part, wherein the at least one RGB-image is preferably taken against a white background. Such RGB-images can be generated by a standard camera or mobile phone.

However, it could also be a hyperspectral image and/or a multispectral image, in which the information density is much higher. Thus, alternatively or in addition, the image data may be based on at least one hyperspectral and/or multispectral image. The latter is preferably in the radiation range between about 390 nm and about 700 nm, in the near infrared range with about 800 nm and in the far infrared range (FIR) with about 820 nm, wherein the at least one multispectral image is preferably taken against a white background. In an example, the multispectral image was taken with at least three spectral channels. In one example, one spectral channel is in a visible spectral range, in a near infrared range and in a far infrared range. However, it is also possible to adopt the radiation range to a specific pathogen or other parameters, like the absorption maxima values of chlorophylls, e.g. which his for chlorophyll a in the red region at 642 nm and in the blue region at 372 nm and for chlorophyll b the values are 626 nm in the red region and 392 nm in the blue region.

In a step S10, image data of a plant or a plant part infested with a pathogen are provided. The image data may be based on at least one RGB-image of the plant and/or the plant part, wherein the at least one RGB-image is preferably taken against a white background. Such RGB-images can be generated by a standard camera or mobile phone. However, it could also be a hyperspectral image and/or a multispectral image, in which the information density is much higher. Thus, alternatively or in addition, the image data may be based on at least one hyperspectral and/or multispectral image. The latter is preferably in the radiation range between about 390 nm and about 700 nm, in the near infrared range (NIR) with about 800 nm and in the far infrared range (FIR) with about 820 nm, wherein the at least one multispectral image is preferably taken against a white background. In an example, the multispectral image was taken with at least three spectral channels. In one example, one spectral channel is in a visible spectral range, in a near infrared range and in a far infrared range. It is further preferred that the image data is based on nine or more images of the plant or plant part, e.g. six side views and three top views of the plant or plant part. It is further preferred that the image(s) are filtered or trimmed or that specific areas of the image(s) are marked before providing the image data. This makes it possible to limit an analysis/the training data to only the relevant parts of a plant. In FIG. 2, such a marking of the image is shown excluding areas from the image data, which appear not relevant for the training data. In FIG. 2, a soybean plant 10 is shown, wherein the pot and the cotyledons (seed leaves) 12 were extracted and not included in the image extraction. Only the primary leaves 14, which have been infested were included in the training data. Trifoliate leaves emerged after inoculation had also been trimmed.

In an example, the digital imaging of the plants, e.g. the in FIG. 2 shown soybean plant, was carried out with an imaging box. The imaging box contained two CCD cameras, which took images in different wavelength ranges. For example, an RGB camera may took images of the plants from a side view ("lateral view") and a multispectral camera may took images of the plant from above ("zenithal view"). The wavelengths of the multispectral camera are preferably in the red-green-blue or visible radiation range with 390 nm to 700 nm, in the near infrared range (NIR) with 800 nm and in the far infrared range (FIR) with 820 nm. However, it is also possible to use one or more hyperspectral images and/or to adopt the radiation range to a specific pathogen or other parameters, like the absorption maxima values of chlorophylls, e.g. which his for chlorophyll a in the red region at 642 nm and in the blue region at 372 nm and for chlorophyll b the values are 626 nm in the red region and 392 nm in the blue region.

In a step S20, genetic result data of the plant or the plant part to which the image data referred are provided. The genetic result data may be obtained by different genetic analysis methods. In this context, it is only important that the genetic result data are based on the plant or plant part referenced in the respective image data. For example, a genetic sequencing method, e.g. real-time quantitative PCR, loop-mediated isothermal amplification or a DNA microarray method. In an example, this involves testing for the presence and the quantity of genetic material in plant samples that can be attributed to a pathogen.

In a step S30, the image data are labeled with the genetic result data, e.g. the image data of the plant or plant part are tagged with the genetic result data. By means of such labeled data, different machine learning models, e.g. deep learning models, may be trained resulting in a very reliable classification algorithm for image classifying a pathogen infestation of a plant.

The present disclosure has been described in conjunction with a preferred embodiment as examples as well. However, other variations can be understood and effected by those persons skilled in the art and practicing the claimed invention, from the studies of the drawings, this disclosure and the claims. Notably, in particular the steps S10 to S30 can be performed in any order, i.e. the present invention is not limited to a specific order of these steps. Moreover, it is also not required that the different steps are performed at a certain place or at one place, i.e. each of the steps may be performed at a different place using different equipment/data processing units. In the claims as well as in the description the word "comprising" does not exclude other elements or steps and the indefinite article "a" or "an" does not exclude a plurality. A single element or other unit may fulfill the functions of several entities or items recited in the claims. The mere fact that certain measures are recited in the mutual different dependent claims does not indicate that a combination of these measures cannot be used in an advantageous implementation.

REFERENCE SIGNS

S10 providing image data of a plant or a plant part infested with a pathogen
S20 providing genetic result data of the plant or the plant part to which the image data referred comprising at least information about type of pathogen
S30 labeling the image data with the genetic result data
10 soybean plant
12 cotyledones (seed leaves)
14 primary leaves
The invention claimed is:

1. A computer-implemented method for generating training data for a machine learning model for image-based detection of a pathogen infestation of a plant, the method comprising:
  providing image data of a plant or a plant part infested with a pathogen;
  performing DNA and/or RNA analysis to obtain genetic result data;
  providing the genetic result data of the plant or the plant part, the genetic result data comprising information about a type of pathogen, the type including at least one of species, subspecies, variety, biotype, or mutant; and
  labeling the image data with the genetic result data, wherein the labeling includes assigning, to the image data, a label representing the type of pathogen based on the genetic result data.

2. The method according to claim 1, wherein the genetic result data further comprises information on a quantity of the pathogen.

3. The method according to claim 1, wherein the image data is based on at least one RGB-image of the plant or the plant part, wherein the at least one RGB-image is taken against a white background.

4. The method according to claim 1, wherein the image data is based on:
  at least one multispectral image, in a radiation range between 390 nm and 850 nm, in a near infrared range with 800 nm and in a far infrared range (FIR) with 820 nm, wherein the at least one multispectral image is taken against a white background; and/or at least one hyperspectral image in a radiation range between 390 nm and 1650 nm.

5. The method according to claim 1, wherein the method further comprises the step of filtering the images, trimming and/or marking specific areas of the images before providing the image data.

6. The method according to claim 1, wherein the genetic result data is based on a quantitative DNA-analysis tool.

7. The method according to claim 1, wherein the pathogen is a fungus.

8. The method according to claim 1, wherein the plant is a soybean plant or a part of a soybean plant and the pathogen is a *Phakopsora pachyrhizi* fungus.

9. A method comprising providing image data of a plant or a plant part infested with a pathogen for use in the computer-implemented method according to claim 1.

10. A method comprising providing genetic result data of a plant or a plant part obtained via DNA and/or RNA analysis, the genetic result data comprising information about a type of pathogen, for use in the computer-implemented method according to claim 1.

11. A method comprising training a machine learning model using training data generated according to the method according to claim 1, wherein the model is configured for image-based detection of pathogen infestation of a plant.

12. A non-transitory computer-readable medium storing a neural network trained with training data generated according to claim 1, wherein training features for the training of the neural network comprise a Normalized Differences Vegetation Index (NDVI) and a Greeness Index (G).

13. A classification system for image classifying a pathogen infestation of a plant, the system comprising:
  processing circuitry configured to:
    provide image data of a plant or plant part;
    feed forward a machine learning algorithm with the image data of a plant or plant part, wherein the machine learning algorithm is trained on the basis of training data provided according to claim 1; and
    output a classification result of a pathogen infestation of the plant.

14. A computer implemented method for image classifying a pathogen infestation of a plant, comprising:
  providing image data of a plant or plant part;
  feeding the machine learning model with the image data of a plant or plant part, wherein the machine learning model is trained on the basis of training data provided according to claim 1; and
  outputting a classification result of a pathogen infestation of the plant.

15. The method according to claim 14, further comprising providing recommendation data for treating the infested plants with an active ingredient and/or a crop protection product suitable for the classified pathogen infestation of the plant.

16. A non-transitory computer-readable medium having instructions encoded thereon that, when executed by a processor, cause the processor to carry out the method of claim 14.

17. The method according to claim 1, wherein the performing DNA and/or RNA analysis to obtain the genetic result data is carried out in-situ.

* * * * *